(12) United States Patent
Curatolo et al.

(10) Patent No.: US 6,548,555 B1
(45) Date of Patent: Apr. 15, 2003

(54) BASIC DRUG COMPOSITIONS WITH ENHANCED BIOAVAILABILITY

(75) Inventors: William J. Curatolo, Niantic, CT (US); James A. S. Nightingale, Bend, OR (US); Ravi M. Shanker, Groton, CT (US); Steven C. Sutton, Niantic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/495,438

(22) Filed: Jan. 31, 2000

Related U.S. Application Data
(60) Provisional application No. 60/119,283, filed on Feb. 9, 1999.

(51) Int. Cl.$^7$ .......................... A61K 47/32; A61K 9/14
(52) U.S. Cl. .................. 514/772.4; 424/488; 424/484; 424/486
(58) Field of Search .................. 514/772.4; 424/488, 424/439, 484, 486

(56) References Cited

U.S. PATENT DOCUMENTS

| | | | |
|---|---|---|---|
| 4,461,759 A | 7/1984 | Dunn | 424/19 |
| 4,758,437 A * | 7/1988 | Sonobe et al. | 424/471 |
| 4,983,593 A | 1/1991 | Miyajima et al. | 514/110 |
| 5,456,923 A | 10/1995 | Nakamichi et al. | 424/489 |
| 5,700,485 A | 12/1997 | Berde et al. | 424/501 |
| 5,707,646 A * | 1/1998 | Yajima et al. | 424/439 |
| 5,723,269 A | 3/1998 | Akagi et al. | 424/497 |

FOREIGN PATENT DOCUMENTS

| | | | |
|---|---|---|---|
| EP | 0231026 | 8/1987 | A61K/31/44 |
| EP | 0280571 | 8/1988 | A61K/9/22 |
| EP | 0852140 | 7/1998 | A61K/9/00 |
| EP | 0901786 | 3/1999 | A61K/9/14 |
| WO | WO9300889 | 1/1993 | A61K/9/16 |
| WO | WO9706781 | 2/1998 | A61K/9/00 |

OTHER PUBLICATIONS

Patent Abstracts of Japan vol. 011, No. 047 (c–403), Feb. 13, 1987 JP 61 212517.

Alan K. Hilton, et al. Jrnl of Pharmaceutical Sciences, vol. 82, No. 7, Jul. 1993 XP–002156064.

P. Giunchedi, et al., Intrnl Jrnl of Pharmaceutics, 85, 1992, 141–147 XP–002074951.

A. Streubel, et al., Jrnl of Controlled Release, 67, 2000, 101–110.

Toshiya Kai, et al., 1996 Pharmaceutical Society of Japan, pp. 568–571.

Lucy S. C. Wan, et al., drug Development and Industrial Pharmacy, 18(9), 997–1011, 1992.

Perry's Chemical Engineers' Handbook Sixth Edition, Robert H. Perry, et al., 1984, 20–54 / 20–57.

Toshio Yamaguchi et al., 1993, vol. 53, No. 4, pp 221–228 (XP002121600).

Takeichi et al., chem. Pharm. Bull, 38(9), 2547–2551, 1990.

Baba, et al., Chem. Pharm. Bull, 38(9), 2542–2546, 1990.

Takeuchi et al., 35 Chem. Pharm. Bull, 3800–3806, 1987.

Dangprasirt et al., 21 Drug Development and Industrial Pharmacy, 2323–2337, 1995.

* cited by examiner

*Primary Examiner*—Thurman K. Page
*Assistant Examiner*—Blessing Fubara
(74) *Attorney, Agent, or Firm*—Peter C. Richardson; Greg C. Benson; James T. Jones

(57) ABSTRACT

A composition comprising a basic drug, a drug which forms a zwitterion, or a salt of either entity, admixed with a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP). The compositions having improved solubility, hence bioavailability, in the small intestine; Processes for testing such compositions, and methods of using such compositions. The compositions comprise the basic drug, zwitterion, or salt and one or more of the aforementioned polymers. The invention further relates to a method for increasing the bioavailability of a basic or a zwitterionic drug comprising co-administering the basic drug, the zwitterionic drug, or the salt, with one or more of the aforementioned polymers.

60 Claims, No Drawings

BASIC DRUG COMPOSITIONS WITH ENHANCED BIOAVAILABILITY

This application is filed claiming priority from Provisional Application No. 60/119,283 filed Feb. 9, 1999.

FIELD OF THE INVENTION

This invention relates to compositions of basic drugs, zwitterionic drugs, or salts of either that have improved solubility, hence bioavailability, in the small intestine, to processes for testing such compositions, and to methods of using such compositions. In particular, it relates to compositions comprising a basic or a zwitterionic drug and a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP). The invention further relates to a method for increasing the bioavailability of a basic or a zwitterionic drug comprising co-administering the basic or zwitterionic drug with any one or more of the aforementioned polymers.

BACKGROUND OF THE INVENTION

It is known in the pharmaceutical arts that low-solubility drugs often show poor bioavailability or irregular absorption, the degree of irregularity being affected by factors such as dose level, fed state of the patient, and form of the drug. A drug which forms a zwitterion can also exhibit poor solubility, depending on its $pK_a$s and on the pH of its aqueous use environment.

Many basic drugs are quite bioavailable, although bioavailability can be dose-dependent. In the low pH environment of the stomach (pH 1–2, usually about 1.2), a basic drug may be soluble. When the drug solution passes into the higher pH environment of the small intestine where the pH is 5 to 7, usually about 6.5, the drug may be above its equilibrium solubility at that pH. However, if the dose is relatively low and if the drug has the capacity to temporarily supersaturate, the drug may maintain supersaturation in the small intestine for a time, thus permitting absorption of the dissolved drug across the intestinal wall. In general, the residence time in the small intestine of humans is around 4 hours. Thus, a drug which can maintain supersaturation at intestinal pH will, in general, be better absorbed than one which does not.

Zwitterionic drugs can be affected by the same considerations. That is, even though a drug forms ions in aqueous use environments having acid and/or basic pHs, and thereby exhibits good solubility in such use environments, the same drug may be poorly soluble in an aqueous use environment having a pH at which the drug assumes its neutral form and the neutral form intrinsically exhibits poor aqueous solubility at that pH.

Some basic and zwitterionic drugs exhibit "dose/solubility-limited exposure". As the dose is increased, the systemic drug exposure increases until a limiting dose is achieved, above which dose the increase in systemic exposure with increasing dose is less than that observed at doses lower than this dose. Since basic and zwitterionic drugs are generally soluble at gastric pH, this effect may be due to precipitation of drug in the small intestine above the limiting dose.

Some basic drugs exhibit little or no capacity to supersaturated at neutral pH; such drugs precipitate quickly in the small intestine even if reasonably soluble in the stomach, and are poorly bioavailable.

It is not generally possible to predict the propensity of a basic drug to supersaturate the small intestinal lumen.

Miyajima et al., U.S. Pat. No. 4,983,593 relates to the destruction of drug crystallinity by drying a solution of drug and polymer. Miyajima discloses, inter alia, formulating HPMCAS with a drug designated as NZ-105. The patent disclosed that there is formed ". . . a composition having a remarkably enhanced bioavailability and easily prepared into tablets, capsules, granules, powders, and the like . . . " The patent teaches that the formulations can be prepared by dissolving NZ-105 and HPMCAS in an organic solvent and removing the solvent by means of vacuum-drying, spray-drying, freeze-drying, or the like, or by coating a filler such as an inorganic salt (e.g., calcium hydrogen phosphate) or a sugar (e.g., lactose, sucrose, and so forth) and the like by means of a fluidized bed granulation method, a centrifugal coating method, or a pan coating method to produce granules.

Nakamichi et al., U.S. Pat. No. 5,456,923, disclose, inter alia, a process for producing solid dispersions by passing a mixture of a drug and a polymer carrier through a twin screw compounding extruder. A large list of polymers which can be used is disclosed.

Miyamoto, PCT/JP96/02246, discloses hydroxypropylmethylcellulose (HPMC), HPMCAS, and poly(vinyl acetate) (PVA) as part of an extensive list of amorphous stabilizers. Miyamoto discloses amorphous dispersions of drug plus amorphism inducing agent plus amorphism stabilizer, formed by heating, milling, or precipitation from a solvent.

U.S. Pat. No. 5,456,923 to Shogo et al. discloses an extrusion method for making solid dispersions. HPMCAS is included in a list of polymeric materials, including materials such as starch or gelatin, that can be used as matrix materials.

Takeichi et al., Chem. Pharm. Bull, 38 (9), 2547–2551 (1990) relates to the destruction of drug crystallinity by co-grinding with other agents. Takeichi attempted to use a solid dispersion of HPMCAS and uracil made by grinding in a ball mill to enhance rectal absorption, but concluded that uracil absorption was lower than for low molecular weight matrix materials such as sodium caprate. The use of HPMCAS was not recommended.

Baba et al., Chem. Pharm. Bull, 38 (9), 2542–2546 (1990) relates to the destruction of drug crystallinity by co-grinding with other agents. Baba made ground mixtures of uracil and HPMCAS along with 50 other matrix materials. Although some enhancement (about a factor of 2) in the dissolution of uracil was observed in the co-ground HPMCAS material relative to a simple mixture of crystalline drug and HPMCAS, the enhancement decreased as the polymer-to-drug ratio was increased. This led the researchers to conclude that HPMCAS adsorbed on the surface of the uracil thereby hindering the dissolution of uracil. Its use was not recommended.

T. Yamaguchi et al., Yakuzaigaku, 53 (4), 221–228 (1993) relates to the destruction of drug crystallinity by spray-drying drug and polymer to form: a dispersion. Yamaguchi prepared solid amorphous dispersions of 4"-O-(4-methoxyphenyl)acetyltylosin (MAT) in HPMCAS as well as carboxymethylethylcellulose (CMEC). Dissolution tests at pH 4.0 showed supersaturated concentrations of MAT 9-fold that of crystalline MAT with HPMCAS dispersions. This concentration was comparable to that obtained with the dissolution of amorphous drug alone. However, the presence of HPMCAS sustained the supersaturation longer than the amorphous drug alone. The authors report that even better results were obtained with the CMEC dispersions, however, causing the authors to conclude that CMEC is the preferred dispersion matrix.

SUMMARY OF THE INVENTION

In a first aspect, this invention provides a composition comprising
   a) a basic drug, a drug which forms a zwitterion, or a salt of either, admixed with
   b) a polymer selected from the group consisting of hydroxypropylmethyl-cellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP);
      wherein, in the absence of said polymer, said basic drug, zwitterionic drug or salt has a solubility in a first aqueous use environment having a pH of 1.0 to 2.0 which is at least 3-fold the solubility of said drug in a second aqueous use environment having a pH in the range of 5.0 to 7.0;
      and wherein, in said composition, said polymer is present in an amount such that, at any time during the first two hours following the time at which said composition has been introduced from said first use environment into said second use environment, the concentration of said dissolved basic drug, zwitterionic drug, or salt of either in said second use environment is increased to at least 1.5-fold, preferably 2-fold, more preferably 5-fold, the concentration of said dissolved basic drug, zwitterionic drug, or salt introduced from said first environment into said second environment in a control composition not containing said polymer.

The term "polymer" as used herein, including the claims, is used as a shorthand notation to refer to any one of hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethyl-cellulose acetate phthalate (HPMCAP), and methylcellulose acetate phthalate (MCAP). The term shall also be understood to mean mixtures of any two or more of the aforementioned polymers.

A preferred subgroup of polymers for use in the invention is HPMCAS, CAT, and CAP. This group of polymers shall be understood to include mixtures of any two or of all three.

Most preferred for use in the invention is HPMCAS.

While not wishing to be bound by theory or mechanism, it is believed that, surprisingly, a simple physical mixture, including a wet or dry granulation, of a basic drug, a zwitterionic drug, or a salt of either, with one or more of the aforementioned polymers, can slow or retard the precipitation of the basic or zwitterionic drug when the pH of a use environment containing such a drug is raised from gastric pH to intestinal pH.

For the sake of convenience, reference hereinafter to a "basic drug" shall be understood as also including zwitterionic drugs and salts of either entity.

A basic drug does not necessarily have to be sparingly soluble at near-neutral pH (pH 5–7) in order to benefit from this invention, although sparingly soluble basic drugs represent a preferred class for use with the invention. Even a basic drug that nonetheless exhibits appreciable solubility at near-neutral pH can benefit from the increased solubility/ bioavailability made possible by this invention if the addition of a polymer further increases its solubility and/or bioavailability, since increasing bioavailability can reduce the size of the dose needed for therapeutic efficacy.

In a further aspect, this invention provides a method of administering a basic drug, a drug which forms a zwitterion, or a salt of either, comprising co-administering, to a patient in need of said drug:
   a) said basic drug, zwitterionic drug, or salt of either, and
   b) a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP);
      wherein, in the absence of said polymer, said basic drug, zwitterionic drug or salt of either has a solubility in a first aqueous use environment having a pH of 1.0 to 2.0 which is at least 3-fold the solubility of said drug in a second aqueous use environment having a pH in the range of 5.0 to 7.0;
      and wherein said polymer is co-administered in an amount such that, at any time during the first two hours following the time at which said basic drug, zwitterionic drug, or salt of either has been introduced from said first use environment into said second use environment, the concentration of said dissolved basic drug, zwitterionic drug, or salt of either in said second use environment is increased to at least 1.5-fold, preferably 2-fold, more preferably 5-fold, the concentration of said dissolved basic drug, zwitterionic drug, or salt introduced from said first environment into said second environment in a control composition not containing said polymer. The method generally improves the solubility of the drug in near-neutral or neutral use environments (pH 5.0–7.0), and also its bioavailability. The amount of polymer is generally such that the improvement in solubility and/or bioavailability lasts for at least fifteen minutes, preferably at least thirty minutes.

It should be noted that the aforementioned polymers do not have the capacity to appreciably solubilize basic or zwitterionic drugs at intestinal pH. As discussed above, and while not wishing to be bound by theory or mechanism, it is believed the polymer is acting to slow the rate of precipitation of such a drug when the drug is initially solubilized (e.g, in the stomach at a pH of 1.0 to 2.0), and then the pre-solubilized drug undergoes a pH increase up to intestinal pH (e.g, as by traveling from the stomach into the small intestine).

The basic drugs suitable for use in this invention can be crystalline or amorphous. Further, the invention has wide applicability and is not limited by or to any particular class of basic drugs. The only types of basic drugs for which the invention may not be as useful are those which, even though they may show a relatively reduced solubility at the pH of the small intestine, are still sufficiently potent to be efficacious because they have (a) an adequate intestinal solubility, (b) an adequate intestinal absorption rate, and (c) a sufficiently low dose, permitting absorption of the complete dose.

The term "drug" in this specification and the appended claims is conventional, denoting a compound having beneficial prophylactic and/or therapeutic properties when administered to an animal, especially a human.

The term "salt" generally means pharmaceutically acceptable salts.

The term "admixed with" refers to the fact that compositions of drug and polymer are simple physical mixtures of the type achieved by combining and physically stirring dry components together. Such physical mixtures include wet and dry granulated mixtures. As is known in the art, granulation is a process used to improve the handling and manufacturing properties of a formulation, for example by increasing particle size to improve flow. Granulation does not substantially change the physical form of the drug such as its crystalline or amorphous character. Granulation is not intended to create an amorphous drug/polymer dispersion.

Compositions comprising dispersions, particularly molecular dispersions, of drug and HPMCAS, as disclosed in the art discussed above, do not form a part of this invention. Thus, compositions made by dissolving a drug plus excipients in a solvent followed by drying from the solvent, or by co-grinding, or by extruding with heating or by other methods do not form a part of this invention.

The term "concentration of said basic dissolved drug, zwitterionic drug, or salt of either" is typically taken as referring to that material that either passes a 0.45 μm syringe filter or, alternatively, the material that remains in the supernatant following centrifugation of a sample. Filtration can be conducted using a 13 mm, 0.45 μm polyvinylidine difluoride syringe filter sold by Scientific Resources under the trademark TITAN®. Centrifugation can be typically carried out in a polypropylene microcentrifuge tube by centrifuging at 13,000 G for 60 seconds. It is recognized that this definition of "dissolved drug" encompasses not only monomeric solvated drug molecules but also a wide range of species that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the: specified dissolution test.

A "sparingly-soluble basic drug" as employed above applies to drugs which are essentially totally water-insoluble or poorly water-soluble at any pH in the range of pH 5.0 to pH 7.0. More specifically, the term applies to any beneficial therapeutic agent which has a dose (mg) to aqueous solubility (mg/ml) ratio greater than 100 ml, where the drug solubility is that of the form or mixture of forms present in the pH range of 5.0 to 7.0. This definition includes but is not limited to basic drugs that have essentially no aqueous solubility (less than 1.0 μg/ml) since the invention can have benefit for such drugs.

A "use environment" as employed herein generally means the gastrointestinal tract if in vivo and aqueous test medium if in vitro. More specifically, "use environment means" (1) if the use environment is in vivo and has a pH in the range of 1.0 to 2.0, the stomach; (2) if the use environment is in vivo and has a pH in the range of 5.0 to 7.0, the small intestine; (3) if the use environment is in vitro and has a pH in either of the ranges just mentioned, aqueous test fluid which is initially at a pH of 1.0 to 2.0 and which is then adjusted to within the range 5.0 to 7.0, as further described below. A composition according to the invention can be tested in vivo or, more conveniently, tested in vitro as further disclosed and discussed below to ascertain whether it is within the scope of the invention.

Similarly, reference to a drug having a "solubility in a first aqueous use environment having a pH of 1.0 to 2.0 which is at least 3-fold the solubility of said drug in a second use environment having a pH in the range of 5.0 to 7.0" means that the equilibrium solubility of the drug at any one or more particular points in the range of 1.0 to 2.0 is 3-fold the equilibrium solubility of the drug at any one or more points in the pH range 5.0 to 7.0. Further, the quoted language refers to a drug which is first dissolved in the first use environment (i.e., of pH 1.0 to 2.0) and then introduced into the second (i.e., pH 5.0 to 7.0) use environment. Thus, if the first use environment is the stomach and the second use environment is the small intestine, the quoted language is understood as meaning the natural transfer of a composition comprising drug and polymer from the stomach to the small intestine. If the first and second use environments are in vitro aqueous fluids, the above quoted language is understood as meaning an aqueous test medium (e.g., such as deionized distilled water) having a pH of 1.0 to 2.0 into which drug and polymer are added, the pH of the said medium then being raised, usually slowly, to the range of 5.0 to 7.0.

"Co-administration" as used herein means that a basic drug can be administered separately from, but within the same general time frame as, polymer. Thus a basic drug can, for example, be administered in its own dosage form which is taken at the same time as the polymer which is in a separate dosage form. If administered separately, it is generally preferred to administer both the basic drug and polymer within 15 minutes of each other, in any order, so that both enter the small intestine at or about the same time. For separate administration, it is most preferred that the basic drug and polymer be administered at essentially the same time.

The basic drug and polymer can also be administered after having been admixed together as a dry composition, for example as part of the same dosage form, and administration as a composition is preferred. The composition can be a simple physical combination, homogeneous or non-homogeneous. Homogeneous compositions are preferred and will often, of necessity, result from the manufacturing process itself, for example where multiple dosage units are to be manufactured from a single production batch and homogeneity must accordingly be ensured. Drug and polymer can be physically admixed, as by stirring the dry components together for formulation, together with other components and excipients as known in the art. The drug and polymer may also be physically admixed by granulating as known in the art, with or without other excipients, utilizing, dry granulation, for example tablet slugging or roller compaction, or by wet granulation, as known in the art.

Whether in the form of a physical mixture or a granulated mixture, a dry composition can be used, together with other components and excipients as known in the art, to manufacture tablets, capsules, powders for oral suspension, and unit dose packets by methods well known to the art. Methods of preparing various oral pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 18th Edition (1990).

Examples of basic drugs which are advantageously formulated with a polymer according to this invention include:
  4-amino-5-(4-fluorophenyl)-6,7-dimethoxy-2-[4-(morpholinocarbonyl)perhydro-1,4-diazepin-1-yl] quinoline
  2-[7-(4-Bromo-2,6-dimethyl-phenyl)-2,5-dimethyl-7H-pyrrolo[2,3-d]pyrimidin-4-ylamino]-butan-1-ol;
  4-(1-Ethyl-propoxy)-3,6-dimethyl-2-(2,4,6-trimethyl-phenoxy)-pyridine;
  4-[3-{4-(2-methylimidazol-1-yl)phenylthio}]phenyl-3,4,5,6-tetrahydro-2H-pyran-4-carboxamide;

[3,6-Dimethyl-2-(2,4,6-trimethyl-phenoxy)-pyridin-4-yl]-(1-ethyl-propyl)-amine;
sertraline; and
ziprasidone Examples of zwitterionic drugs which are advantageously formulated with a polymer according to this invention are:

(4-{2-[2-Hydroxy-2-(2-trifluoromethyl-thiazol-4-yl)-ethylamino]-propyl}-phenoxy)-acetic acid; and 7-(6-Amino-3-aza-bicyclo[3.1.0]hex-3-yl)-1-(2,4-difluoro-phenyl)-6-fluoro-4-oxo-1,4-dihydro-[1,8] naphthyridine-3-carboxylic acid.

A composition of matter according to the invention is within the scope of the invention if, when the composition is tested in vivo, the Cmax achieved with said composition is at least 1.25-fold, preferably at least 1.5-fold, more preferably at least 2-fold the Cmax achieved with a control composition (as disclosed below) comprising an equivalent quantity of a basic or zwitterionic drug or salt of either, e.g., a composition lacking polymer. Cmax is well understood in the art as an abbreviation for the maximum drug concentration in serum or plasma of the test subject. In vivo testing protocols can be designed in a number of ways. By measuring the Cmax for a population to which the test composition has been administered and comparing it with the Cmax for the same population to which the control has also been administered, the test composition can be evaluated.

Compositions according to the invention also include those which exhibit at least a 1.25-fold, preferably at least a 1.5-fold, more preferably at least a 2-fold improvement in AUC over a control not containing polymer. AUC is a determination of the area under the curve (AUC) plotting the serum or plasma concentration of drug along the ordinate (Y-axis) against time along the abscissa (X-axis). Generally, the values for AUC represent a number of values taken from all the subjects in a patient test population and are, therefore, mean values averaged over the entire test population. By measuring the AUC for a population to which the test composition has been administered and comparing it with the AUC for the same population to which the control has been administered, the test composition can be evaluated. Alternatively, the AUC test/AUC control ratio may be determined for each subject, them averaged. AUC's are well understood, frequently used tools in the pharmaceutical arts and have been extensively described, for example in "Pharmacokinetics Processes and Mathematics", Peter E. Welling, ACS Monograph 185; 1986.

Thus, a composition is within the scope of the invention if it effects in vivo either a Cmax or an AUC that is at least 1.25 times, preferably at least 1.5 times, more preferably at least 2.0 times the corresponding Cmax or AUC exhibited by a control composition comprising: an equivalent quantity of drug and excipients, but without polymer. In a preferred embodiment, compositions according to the invention, in addition to displaying at least a 1.25-fold improvement in Cmax as discussed above, also exhibit at least a 1.25-fold improvement in AUC.

Preferred compositions are those which effect a coefficient of variation of Cmax or AUC which is at least 10% less than the coefficient of variation of Cmax and/or AUC observed for a control composition comprising an equivalent quantity of drug and excipients, but without polymer. "Coefficient of variation" as used here has its standard meaning, i.e., the ratio of the standard deviation to the mean value for Cmax or AUC. Especially preferred compositions exhibit a coeffient of variation for both Cmax and for AUC which is at least 10% less than the corresponding coefficients of variation for Cmax and AUC observed for said control composition.

Cmax and AUC can be determined in humans or a suitable animal model, such as dogs. If a composition comprising a basic or zwitterionic drug, or a salt of either, admixed with polymer, increases Cmax or AUC by 25% in any species, it is within the scope of the invention.

A drug can be tested in vitro to determine if it exhibits an equilibrium solubility in a pH 1.0 to 2.0 use environment that is at least 3-fold its equilibrium solubility in a pH 5.0 to 7.0 environment. A test drug is dissolved in a pH 1–2 environment, typically aqueous deionized distilled water adjusted to a target pH within the aforesaid pH 1–2 range by adding an appropriate amount of hydrochloric acid. The amount of drug added is an amount sufficient to saturate the aqueous test medium. The test medium can be agitated, typically gently, by means of a stirring bar, overhead stirrer, or the like. Typically the test medium is left to sit (while being agitated) for several hours, typically overnight. The sample can then be filtered or centrifuged as previously described, and solubility in the filtrate or supernate can then be measured by determining the concentration with any suitable means of detection appropriate to the drug. Likewise, the solubility is also determined at pH 5 to 7. If the drug's pH 1–2 solubility is 3- or more-fold its pH 5–7 solubility, then the drug will benefit from this invention.

A composition can also be tested in vitro to determine whether it is within the scope of the invention. A typical test can be described as follows for a planned dosage form. A quantity of basic drug, zwitterionic drug, or salt of either, usually on the order of 1–5 mg, is dissolved in, as the test medium, an aqueous use environment having a pH of 1.0–2.0, usually 5–40 mL. Generally a single pH within the range, for example a pH of 1.2, is chosen for consistency in results and to facilitate comparison. The drug composition may or may not dissolve completely. The aqueous environment is, as disclosed above, typically deionized, distilled water with sufficient aqueous hydrochloric acid added to adjust the pH to 1.0–2.0. Acid having a normality of 1 to 4 is usually sufficient for adjusting the pH to within 1.0 to 2.0, although a higher concentration can be used if desired. Sufficient acid is present in the test medium such that at least a portion of the drug dissolves while still maintaining the pH of the test medium within a range of 1.0–2.0. It is desirable to agitate the test medium, as by using a stirring bar or an overhead stirrer, and the medium is allowed to stir up to several hours or longer, if desired. An identical drug-containing control sample should be made in the same manner or, alternatively, the drug containing sample test medium already made can, before the addition of any polymer, be split into two equal portions, one being reserved as the control, the other as the test sample. At this point a quantity of test polymer should be added to the test sample in proportion to its intended presence in the final composition. Polymer is omitted from the control sample, although other (non-polymer) excipients can be added.

Control and test can then be adjusted up, as by slow titration, to a standard pH between 5.0 and 7.0, a standard target pH usually being chosen, for example pH 6.5. Titration with aqueous base (or other method of pH adjustment) should be effected over a timespan slow enough, and with a concentration of base dilute enough, so that local precipitation of the drug from solution is minimized, and also to roughly mimic the physiology of gastric emptying into the small intestine. Usually titration using 0.1 to 1 N sodium (or potassium) hydroxide for coarse or rapid pH adjustment in conjunction with 0.01 to 0.1 N sodium (or potassium) hydroxide for fine pH adjustment is effected over a timespan of at least 5 minutes, more preferably over 10 or even 15 minutes. The sample and control can then be filtered (or centrifuged) and the filtrate (or supernate) analyzed by any convenient technique suitable to the drug being tested, such as HPLC, GC, and so forth, using appropriate detection. If the concentration detected at pH 5.0 to 7.0 in the presence of polymer is at least 1.5 times the concentration of that in the control at any time during the 2 hours following titration to pH 5 to 7, the composition or dosage form is within the scope of the invention.

The above test can also be conducted for a pre-formed or pre-manufactured dosage (e.g., a tablet or capsule) already containing polymer. The test is as described above, with a few modifications. First, it may be necessary to pulverize the dosage form if it is a tablet. If the dosage form is a capsule or a powder for oral suspension, then the capsule fill or powder may be tested directly. Since a pre-formed test sample contains test polymer, it will not be possible to split the initial sample into a test portion and control portion. It may accordingly be necessary to make a like composition less the polymer to function as a control. Alternatively, if none of the excipients influences solubility, the control can consist of drug alone, i.e., no other excipients. Generally, initial identical aqueous test medium solutions having a pH of 1.0 to 2.0 should be made, or divided as aliquots out of a common stock, and set aside. Identical quantities of test and control compositions can be added to each and then treated in parallel, as described above.

Thus a composition which is within the scope of this test is one which comprises a basic drug, a zwitterionic drug, or a salt of either, admixed with a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP).

wherein, when said composition is dissolved in an aqueous in vitro test medium having a pH of 1.0 to 2.0, and said test medium is then adjusted to a pH between 5.0 and 7.0, the concentration of said drug in said aqueous pH 5–7 test medium, at any time during the first two hours following said pH adjustment, is at least 1.5-fold the concentration of said drug in a control aqueous test medium containing no polymer.

Compositions within the above in vitro test are provided as a further aspect of the invention.

Compositions are within the scope of the invention if they pass either the in vitro or the in vivo test.

DETAILED DESCRIPTION OF THE INVENTION AND PREFERRED EMBODIMENTS

Synthesis of HPMCAS can be conducted by treating O-(hydroxypropyl)-O-methylcellulose with acetic anhydride and succinic anhydride, as set forth in Tezuka et al, Carbohydrate Research 222(1991)255–259 and in Onda et al, U.S. Pat. No. 4,385,078, the teachings of which are incorporated herein by reference. Although such derivatives of cellulose are often considered in the literature as simply having varying average amounts of the four substituents attached to the three hydroxyl groups on each of the glucose repeat units of cellulose, $^{13}$C-NMR research suggests that most of the hydroxyl groups initially present on the 2-hydroxypropyl groups are substituted by methyl, acetyl, succinyl, or a second 2-hydroxypropyl group, see U.S. Pat. No. 4,385,078. Although essentially any degree of substitution of the various groups can be used as long as the resulting polymer is soluble at the pH of the small intestine, e.g., pH 5 to 7, the amounts of the substituents methoxy, hydroxypropoxy, acetyl, and succinyl, are generally in the range of 10 to 35 wt %, 3 to 15 wt %, 3 to 20 wt %, and 2 to 30 wt %, respectively. Preferably, the amounts of the substituents are 15 to 30 wt %, 4 to 11 wt %, 4 to 15 wt %, and 3 to 20 wt %, respectively.

Alternatively, HPMCAS, and all of the other aforementioned polymers, may easily be purchased in a number of grades from a number of commercial suppliers such as Eastman Chemical: Co., Kingsport, Tenn.; and Shin Etsu, Tokyo, Japan. For example, HPMCAS is available from Shin Etsu in at least six different grades (LF, MF, HF, LG, MG, HG).

The amount of polymer incorporated into a composition according to the invention is from 1 mg to 10 g per dose for an adult human, preferably 10 mg to 2 g, more preferably 20 mg to 1 g. It is desirable to achieve as high a concentration of polymer in the small intestine as possible, within the practical limits of size for an oral dosage form. For example, if one assumes an availability of approximately 100 mL of fluid in the small intestine, then 200 mg of polymer will form a 2 mg/mL solution. The in vitro test may be used to approximate an appropriate amount of polymer to inhibit precipitation of a particular drug.

Although the key ingredients present in compositions of the present invention can be simply the basic drug to be delivered and polymer, the inclusion of other excipients in the composition may be useful and even preferred. For example, excipients which aid in dosage form disintegration or drug wetting and dissolution or efficient formulation flow or efficient tabletting may be included.

Another type of excipient useful as a component of the compositions herein is a surface-active agent such as a fatty acid and alkyl sulfonate; commercial surfactants such as those sold under tradenames such as benzethanium chloride (Hyamine® 1622, available from Lonza, Inc., Fairlawn, N.J.), docusate sodium (available from Mallinckrodt Spec. Chem., St. Louis, Mo.), polyoxyethylene sorbitan fatty acid esters (Tween®, available from ICI Americas Inc, Wilmington, Del.), Liposorb® P-20 (available from Lipochem Inc, Patterson, N.J.), Capmul® POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can be employed advantageously to increase the rate of dissolution by facilitating wetting, thereby increasing the maximum drug concentration and the degree of supersaturation attained, and also to inhibit crystallization or precipitation of drug by interacting with dissolved drug by mechanisms such as complexation, formation of inclusion complexes, formation of micelles or adsorbing to the surface of solid drug, crystalline or amorphous. These surface active agents may typically comprise up to 25% of the composition.

In addition to mixtures of drug and polymer (and other excipients as discussed immediately above), other conventional formulation excipients can be employed in the compositions of this invention, including those excipients well known in the art. Generally, excipients such as fillers, disintegrating agents, pigments, binders, lubricants, flavorants, and so forth can be used for customary purposes and in typical amounts without affecting the properties of the compositions. These excipients may be mixed or granulated with drug and polymer, or may be added after drug and polymer are mixed or granulated, in order to formulate the composition into tablets, capsules, suspensions, powders for suspension, and the like.

Compositions can also be tested in vivo in dogs as follows:

Beagle dogs (typically n=4–6) that have been fasted the previous day are administered the test or control composition in the fasted or fed state (fasted state: no food is allowed until after an 8 hr blood sample; fed state: a meal of 14 g of dry dog food and 8 g of olive oil (this meal imitates the high fat "FDA breakfast") immediately before dosing test or control composition, and regular rations after the 8 hr sample).

The test and control compositions are administered, via oral gavage in water or 0.2% aqueous polysorbate 80 to aid in wetting, through PE205 tubing attached to a syringe. Dogs are returned to metabolism cages with normal access to water. Alternatively, dosing may be via capsules or tablets. Test and control formulations can be identical except for the presence or absence of polymer. Alternatively, the control formulation can consist of drug alone.

Blood samples are taken from the jugular vein using a 10 ml disposable syringe with a 20 gauge needle at 0.5, 1, 1.5, 2, 3, 4, 6, 8 (and occasionally 12 hr) hours post dose. Other sampling times may be used with the conditions that $T_{max}$ is bracketed by the sampling intervals and that an accurate AUC may be calculated. Samples are immediately transferred to clean glass culture tubes containing heparin. Samples are centrifuged at room temperature at 3000 rpms for 5 minutes. Plasma is transferred to clean glass 1 dram vials using a 5 ¼" (13 cm) Pasteur pipette. Plasma samples are frozen on dry ice and stored in a laboratory freezer until assayed by HPLC.

From plasma or serum drug concentrations, typical pharmacokinetic parameters, such as $C_{max}$, $T_{max}$ and AUC are calculated for each dog, and then averaged for the test population.

Test compositions or controls can be tested in vivo in humans as follows. In a crossover design, 4 or more healthy human subjects are dosed with a suspension of crystalline drug (or amorphous drug if the drug does not crystallize) or a suspension of the drug/polymer composition. Blood samples are taken before dosing and at a variety of times post-dosing, with the number and temporal distribution of sampling times chosen to bracket $T_{max}$ and permit accurate measurement of AUC. Drug concentration in plasma or serum is measured by an appropriate assay, and $C_{max}$, $T_{max}$, and AUC are determined. A composition of this invention is a composition comprising a basic drug, a zwitterionic drug, or a salt of either, admixed with polymer, as previously discussed, which, when tested in vivo:

(a) exhibits a drug $C_{max}$ which is greater than 1.25-fold the $C_{max}$ determined after dosing said drug, zwitterion, or salt in a control composition not containing polymer; or (b) exhibits a drug AUC which is greater than 1.25-fold the AUC determined after dosing said drug, zwitterion, or salt in a control composition not containing polymer.

Preferred drug/polymer compositions are those which satisfy both the (a) and (b) criteria above.

Compositions of this invention can be used in a wide variety of forms for administration of drugs orally, usually together with a pharmaceutically acceptable diluent or carrier. Exemplary dosage forms are powders or granules that can be taken orally either dry or reconstituted by addition of water to form a paste, slurry, suspension or solution; tablets, capsules, or pills. Various additives can be mixed, or granulated with the compositions of this invention to form a material suitable for the above dosage forms. Potentially beneficial additives fall generally into the following classes: other matrix materials or diluents, surface active agents, drug complexing agents or solubilizers, fillers, disintegrants, binders, lubricants, and pH modifiers (e.g., acids, bases, or buffers).

Examples of other matrix materials, fillers, or diluents include lactose, mannitol, xylitol, microcrystalline cellulose, calcium diphosphate, and starch.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch gycolate, sodium alginate, carboxymethyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Examples of pH modifiers include acids such as citric acid, acetic acid, ascorbic acid, lactic acid, aspartic acid, succinic acid, phosphoric acid, and the like; and buffers generally comprising mixtures of acids and the salts of said acids.

In addition to the above additives or excipients, use of any conventional materials and procedures for formulation and preparation of oral dosage forms using the compositions of this invention known by those skilled in the art can be useful.

The exact dose of composition administered will, of course, differ depending on the specific basic drug of interest, on the subject being treated, on the severity of the condition being treated, on the route of administration and on the judgment of the prescribing physician.

As previously mentioned, for oral administration a pharmaceutical composition suitable for use in this invention can take various forms, including solutions, suspensions, tablets, pills, capsules, powders, and the like. Tablets may contain various excipients such as the matrix materials, fillers, diluents, surface active agents, drug complexing agents, solubilizers, disintegrants, binders, lubricants, and pH modifiers exemplified above. Hard gelatin capsule formulations generally comprise drug, polymer, and excipients as described above for tablets. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

Other features and embodiments of the invention will become apparent by the following examples which are given for illustration of the invention rather than limiting its intended scope.

EXAMPLE 1

This example discloses an in vitro dissolution test. In this method the concentration of test compound in solution is determined as a function of time. Test mixture resides in a glass beaker from which samples are taken and expelled through a filter at pre-determined time points. In between sampling, the contents of the beaker are stirred at ambient room temperature. The Mettler DL21 Titrator apparatus was calibrated for pH readings from pH 1 to pH 7 as described in the equipment manual.

Into one "small" glass beaker (cat # 23516, Mettler—Toledo, for sample volumes 10–20 ml), 10 ml deionized water was added, and the pH adjusted to between pH 1 and 2, with 10 M HCl. A solution of compound was made by dissolving 1 mg of the hydrochloride salt of 2-[7-(4-Bromo-2,6-dimethyl-phenyl)-2,5-dimethyl-7H-pyrrolo[2,3-d]pyrimidin-4-ylamino]-butan-1-ol (compound 1) in pH 1–2 water. The compound solution was stirred using the overhead stirrer (Mettler DL21 Titrator apparatus, setting 2) for 5 min. During this time the pH remained in the range of 1–2. (final concentration: 0.1 mg/ml).

The mixture was then equally divided into two small glass beakers each containing a magnetic stir bar. While continuously stirring (overhead stirrer, setting 2, Mettler Titrator), the pH of the "control" mixture was increased to pH 6.5 with 0.1 M and 0.01 M NaOH (time=0, 0.1 mg/ml compound concentration). The beaker containing the control mixture was then covered with parafilm, and moved to a stirring plate, where it was continuously stirred for 2 hr at ambient room temperature (setting 1.5, VWR Scientific model 220 Mini-Hot Plate/Stirrer). The contents of each beaker were transferred to a 2 dram screw-capped glass vial and from 2–24 hr were agitated at ambient room temperature using a Labquake (cat# C415-110).

The following polymers were examined in separate experiments: hydroxypropyl methyl cellulose acetate succinate (HPMCAS), polyvinyl alcohol (PVA), hydroxypropyl methyl cellulose (HPMC) and polyvinylpyrrolidone (PVP). The "polymer" mixture was made by adding 1.0 mg of one the above polymers to the remaining glass beaker, and stirred for 5 min. (overhead stirrer, setting 2) (theoretical polymer concentration: 0.1 mg/ml). The pH of the polymer mixture was then similarly increased to pH 6.5 (time=0, 0.1 mg/ml compound concentration). The beaker containing the polymer mixture was then similarly covered with parafilm, and moved to the stirring plate, where it was continuously stirred for 2 hr at ambient room temperature (setting 1.5). After transfer to 2 dram screw-capped glass vials, the test and control were agitated from 2–24 hr at ambient room temperature using a Labquake.

For 5 min. before the specified sampling time the sample was agitated by overhead stirring, and the pH of control and polymer mixtures were measured. Samples (≈1 ml) were taken at 1, 2 and 24 hr using a glass Pasteur pipet. Each sample was transferred into a 1.0 ml plastic syringe with a Gelman Acrodisc 1.2 μm syringe filter attached. The sample was then expelled through the filter into a glass HPLC injection vial, capped, assayed by HPLC using a ZORBAX® (Registered Trademark of the DuPont Company) $R_x$C-18 column (15 cm) at ambient room temperature, 1 ml/min. flow rate (CONSTAMETRIC® 4100 pump), with an isocratic mobile phase consisting of 46% acetonitrile, 10% isopropanol, and 44% water 50 mM in acetic acid and containing 0.1% triethylamine, and compound concentration calculated.

The concentration of compound in the control filtrate as a function of elapsed time (time=0 when the pH was first raised to 6.5) was found to be 0.016 mg/ml at 1 hr., 0.019 mg/ml at 2 hr. and 0.014 mg/ml at 24 hr. (see Table 1-1). The concentration of compound in the HPMCAS filtrates as a function of elapsed time was found to be 0.066 mg/ml at 1 hr, 0.063 mg/ml at 2 hr and 0.049 mg/ml at 24 hr. (see Table 1-1). HPMCAS, HPMC, and PVA effected useful increases in drug concentration, with HPMCAS being the most effective of the three. The other 3 polymers tested in this example did not result in compound concentrations nearly as high as those in the HPMCAS mixture. This result showed that HPMCAS was preferred among the polymers tested.

TABLE 1-1

| Polymer | Compound 1 Concentration (mg/ml) | | | |
|---|---|---|---|---|
| | 0 hr | 1 hr | 2 hr | 24 hr |
| CONTROL | 0.1 | 0.016 | 0.019 | 0.014 |
| HPMCAS | 0.1 | 0.066 | 0.063 | 0.049 |
| HPMC E3 | 0.1 | 0.054 | 0.037 | 0.01 |
| PVP | 0.1 | 0.033 | 0.015 | 0.01 |
| PVA | 0.1 | 0.056 | 0.023 | 0.007 |

EXAMPLE 2

This example follows the same procedure as Example 1, except the compound and polymer concentrations were different.

Into one "small" glass beaker (cat # 23516, Mettler—Toledo, for sample volumes 10–20 ml), 10 ml deionized water was added, and the pH adjusted to between pH 1 and 2, with 10 M HCl. A solution of compound was made by dissolving 10 mg of Compound 1 in pH 1–2 water. The compound solution was stirred using the overhead stirrer (Mettler DL21 Titrator apparatus, setting 2) for 5 min. During this time the pH remained in the range of 1–2. (final concentration: 1.0 mg/ml).

The mixture was then equally divided into two small glass beakers each containing a magnetic stir bar. While continuously stirring (overhead stirrer, setting 2), the pH of the "control" mixture was increased to pH 6.5 with 0.1 M and 0.01 M NaOH (time=0, 1.0 mg/ml compound concentration). The beaker containing the control mixture was then covered with parafilm, and moved to a stirring plate, where it was continuously stirred for 2 hr at ambient room temperature (setting 1.5, VWR Scientific model 220 Mini-Hot Plate/Stirrer). From 2–24 hr the samples were agitated at ambient room temperature in 2 dram screw-capped glass vials using: a Labquake (cat# C415-110).

Only HPMCAS was examined in this example. The "polymer" mixture was made by adding 10 mg of polymer to the remaining glass beaker, and stirred for 5 min. (overhead stirrer, setting 2) (theoretical polymer concentration: 2 mg/ml). The pH of the polymer mixture was then similarly increased to pH 6.5 (time=0, 1.0 mg/ml compound concentration). The beaker containing the polymer mixture was then similarly covered with parafilm, and moved to the stirring plate, where it was continuously stirred for 2 hr at ambient room temperature (setting 1.5). From 2–24 hr the samples were agitated at ambient room temperature in 2 dram screw-capped glass vials using the Labquake.

For 5 min. before the specified sampling time the sample was agitated by overhead stirring, and the pH of control and polymer mixtures were measured. Samples (≈1 ml) were taken at 1, 2 and 24 hr using a glass Pasteur pipet. Each sample was transferred into a 1.0 ml plastic syringe with a Gelman Acrodisc 1.2 μm syringe filter attached. The sample was then expelled through the filter into a glass HPLC injection vial, capped, assayed by HPLC, and compound concentration calculated.

The concentration of compound in the control filtrate as a function of elapsed time (time=0 when the pH was first raised to 6.5) was found to be 0.008 mg/ml at 1 hr., 0.005 mg/ml at 2 hr. and 0.003 mg/ml at 24 hr. (see Table 2-1). The concentration of compound in the HPMCAS filtrates as a function of elapsed time was found to be 0.585 mg/ml at 1 hr, 0.473 mg/ml at 2 hr and 0.231 mg/ml at 24 hr. (see Table 2-1). This result showed that HPMCAS maintained compound concentration at even higher levels.

TABLE 2-1

| Polymer | Compound 1 Concentration (mg/ml) | | | |
| --- | --- | --- | --- | --- |
| | 0 hr | 1 hr | 2 hr | 24 hr |
| CONTROL | 1.0 | 0.008 | 0.005 | 0.003 |
| HPMCAS | 1.0 | 0.585 | 0.473 | 0.231 |

EXAMPLE 3

Capsules (size #2) were prepared containing 10 mgA ziprasidone hydrochloride (Z) as either a 1:5 (w/w) Compound Z/HPMCAS physical mixture (HPMCAS Formulation) or without HPMCAS (Control Z). The capsule fill compositions are presented in Table 3-1.

Dogs were dosed after an overnight fast, followed immediately by an oral gavage of 50 ml of tap water. Blood (3 ml) was collected from the jugular vein pre-dosing and at 0.5, 1, 1.5, 2, 3, 4, 6, and 8 hour post-dosing.

To 0.5 ml of a plasma sample, 10 µl of a 100µg/ml solution of an internal standard 5-[2-(4-Naphthalen-1-yl-piperazin-1-yl)-ethyl]-1,3-dihydro-indol-2-one (Lowe III, J. A., T. F. Seeger, A. A. Nagel, H. R. Howard, P. A. Seymour, J. H. Heym, F. E. Ewing, M. E. Newman, A. W. Schmidt, J. S. Furman, L. A. Vincent, P. R. Maloney, G. L. Robinson, L. S. Reynolds, and F. J. Vinick, 1-*Naphthylpiperazine Derivatives as Potential Atypical Antipsychotic Agents. Journal of Medicinal Chemistry*, 1991. 34(6): p. 1860–66) prepared in methanol/water, and 7.0 ml of methyl-t-butyl ether was added, and the sample was mechanically shaken for 10 minutes and then centrifuged for 10 minutes at 3,000 rpm and room temperature. The organic layer was separated, and evaporated to dryness. The sample was then reconstituted with 200 µl of mobile phase composed of 40% of a 5 mM NaH2PO4 buffer and 60% acetonitrile. Analysis was carried out by HPLC, using a Chromaega CN&NP column (25 cm, 5 micron particle size, ES Industries, West Berlin, N.J.), at room temperature, at a flow rate of 1.5 ml/min (Spectraphysics ConstaMetric 4100 pump), and detected at 315 nm (LDC Spectromonitor 3200, Acton, Mass.). The retention times of ziprasidone and internal standard were 10.3 and 14.6 min, respectively. Quantification was effected by measuring the peak ratio of ziprasidone to internal standard and reference to a calibration curve. The assay was linear up to 1000 ng/ml with a limit of reliable detection of 10 ng/ml. Inter-assay accuracy and precision values were ≈10% and ≈11%, respectively.

Pharmacokinetic data are presented in Table 3-2. $C_{max}$ is the maximum observed plasma Compound Z concentration, averaged over the number of dogs dosed with each formulation. $AUC_{0-8}$ is the average area under the plasma Compound Z concentration vs. time curve from 0 to 8 hours.

These data demonstrate that the physical mixture of HPMCAS and Compound Z, when orally dosed to beagle dogs, gave a higher systemic Compound Z exposure than after dosing the Compound Z alone.

TABLE 3-1

Formulations studied in the beagle dog.

| Component | HPMCAS (% w/w) | Control Z (% w/w) |
| --- | --- | --- |
| ziprasidone HCl | 7.5 | 30.2 |
| HPMCAS | 37.4 | — |
| lactose monohydrate | 24.5 | — |
| lactose hydrous | — | 58.6 |
| microcrystalline cellulose[1] | 20.4 | — |
| sodium lauryl sulfate | 2.0 | — |
| sodium starch glycolate[2] | 8.2 | — |
| pregelatinized starch[3] | — | 10.0 |
| magnesium stearate | — | 1.2 |

[1]Avicel PH102 ®
[2]Explotab ®
[3]starch 1500

TABLE 3-2

Canine pharmacokinetics after oral dosing of Compound Z formulation.

| Formulation | Dose[1] (mg) | n[2] | $C_{max}$ (ng/ml) | $AUC_{0-8}$ (ng-hr/ml) |
| --- | --- | --- | --- | --- |
| Control | 10 | 9 | 58.7 | 276.2 |
| HPMCAS | 10 | 10 | 85.8 | 440.0 |

[1]For comparison purposes, the average weight of beagle dogs used in this study was around 10 kg.
[2]Number of dogs studied.

EXAMPLE 4

This example discloses an in vitro dissolution test with another drug. In this method the concentration of test compound in solution is determined as a function of time. Test mixture resides in a glass beaker from which samples are taken and expelled through a filter at pre-determined time points. In between sampling, the contents of the beaker are stirred at ambient room temperature. The Mettler DL21 Titrator apparatus was calibrated for pH readings from pH 1 to pH 7 as described in the equipment manual.

Into one "small" glass beaker (cat # 23516, Meffler—Toledo, for sample volumes 10–20 ml), 20 ml deionized water was added, and the pH adjusted to between pH 1 and 2, with 10 M HCl. A solution of compound was made by dissolving 100 mgA (milligrams of active drug as the non-salt) of 4-[3-{4-(2-methylimidazol-1-yl)phenylthio}] phenyl-3,4,5,6-tetrahydro-2H-pyran-4-carboxamide, methanesulfonate (mesylate) salt (Compound 2) in pH 1–2 water. The compound solution was stirred using the overhead stirrer (Mettler DL21 Titrator apparatus, setting 2) for 5 min. During this time the pH remained in the range of 1–2. (final concentration: 5 mgA/ml).

The mixture was then equally divided into two small glass beakers each containing a magnetic stir bar. While continuously stirring (overhead stirrer, setting 2), the pH of the "control" mixture was increased to pH ~6.8 with 0.1, M and 0.01 M NaOH (time=0, and 5 mg/ml compound concentration). The beaker containing the control mixture was then covered with parafilm, and moved to a stirring plate, where it was continuously stirred for 4 hr at ambient room temperature (setting 1.5, VWR Scientific model 220 Mini-Hot Plate/Stirrer). From 4–24 hr the samples were agitated at ambient room temperature in 2 dram screw-capped glass vials using a Labquake (cat# C415-110).

The "polymer" mixture was made by adding 10 mg of HPMCAS-LF to the remaining glass beaker containing 10 ml of compound solution, and stirred for 5 min. (overhead stirrer, setting 2) (theoretical polymer concentration: 1 mg/ml). The pH of the polymer mixture was then similarly increased to pH ~6.8 (time=0, and 5 mgA/ml compound concentration). The beaker containing the polymer mixture was then similarly covered with parafilm, and moved to the stirring plate, where it was continuously stirred for 4 hr at ambient room temperature (setting 1.5). From 4–24 hr the samples were agitated at ambient room temperature in 2 dram screw-capped glass vials using the Labquake.

For 5 min. before the specified sampling time the sample was agitated by overhead stirring, and the pH of control and polymer mixtures were measured. Samples (≈1 ml) were taken at 1, 2, 3, 4 and 24 hr using a glass Pasteur pipet. Each sample was transferred into a 1.0 ml plastic syringe with a Gelman Acrodisc 1.2 μm syringe filter attached. The sample was then expelled through the filter into a glass HPLC injection vial, capped, assayed by HPLC, and compound concentration calculated.

HPLC Conditions for in vitro example (two injections per sample): Column: Zorbax C8 Reverse Phase, 5 μm, 4.6×150 mm Flow rate: 1.0 ml/min Injection volume: 20 μl Detection: UV @ 264 nm Retention time: ~16 minutes Mobile phase: 77% 0.2% TFA 18% ACN: 5% 2-Propanol Column Temperature: 30° C.

The concentration of Compound 2 in the control filtrate as a function of elapsed time (time=0 when the pH was first raised to 6.8) was found to be 0.021 mg/ml at 1 hr., 0.007 mg/ml at 2 hr., 0.009 mg/ml at 3 hr., 0.006 mg/ml at 4 hr. and 0.004 mg/ml at 24 hr. (see Table 4-1). The concentration of compound in the HPMCAS filtrates as a function of elapsed time was found to be 0.046 mg/ml at 1 hr., 0.052 mg/ml at 2 hr., 0.047 mg/ml at 3 hr., 0.051 mg/ml at 4 hr. and 0.036 mg/ml at 24 hr. (see Table 4-1). This result showed that HPMCAS maintained compound concentration at higher levels than controls.

TABLE 4-1

| Polymer | Compound 2 Concentration (mg/ml) | | | | | |
|---|---|---|---|---|---|---|
| | 0 hr | 1 hr | 2 hr | 3 hr | 4 hr | 24 hr |
| CONTROL | 5.0 | 0.021 | 0.007 | 0.009 | 0.006 | 0.004 |
| HPMCAS | 5.0 | 0.046 | 0.052 | 0.047 | 0.051 | 0.036 |

EXAMPLE 5

Suspensions were prepared containing 50 mgA Compound 1 as either a 1:10 (w/w) Compound 1/HPMCAS physical mixture (HPMCAS Formulation) or without HPMCAS (Control). The suspension compositions are presented in Table 5-1.

After overnight fast dogs were dosed with 30 ml of the suspension, via a gavage tube directly into the stomach. Blood (5 ml) was collected from the jugular vein predosing and at 0.25, 0.5, 1, 2, 3, 4, 6, 8, 12 and 24 hour post-dosing.

Drug concentrations in plasma were analyzed by reverse-phase high performance liquid chromatography at a flow rate of 1 mL/min using a Zorbax Rx C-8 column (4.6 mm×150 mm), and a UV detector (230 nm).

Aliquots consisting of 1000 μL of plasma; 100 μL of internal standard (200 μg/mL in acetonitrile), and 200 μL of a 1 N sodium hydroxide were extracted into 5 mL of methyl-t-butyl ether (MTBE). The samples were subsequently vortexed for 30 seconds and centrifuged for 2 minutes (2000 rpm). The organic layer was transferred to clean disposable culture tubes and evaporated to dryness in an Evapotech evaporator. Dried down samples were reconstituted in 200 L of mobile phase (46% acetonitrile; 10% isopropanol; 44% 0.5 M acetic acid; 0.1% TEA) and injected onto the column in 20 μL aliquots. The linear dynamic range of the assay was from 0.20 μg/mL (LLQ) to 50 μg/mL, unless stated otherwise.

Pharmacokinetic data are presented in Table 5-2. $C_{max}$ is the maximum observed plasma Compound 1 concentration, averaged over the number of dogs dosed with each formulation. $AUC0_{0-24}$ is the average area under the plasma Compound 1 concentration vs. time curve from 0 to 24 hours.

These data demonstrate that the physical mixture of HPMCAS and Compound 1, when orally dosed to a beagle dog, gave a higher systemic Compound 1 exposure than after dosing the Compound 1 alone. The data also shows that the invention reduced the coefficient of variation (CV), i.e. standard deviation divided by mean, in the pharmacokinetic parameters.

TABLE 5-1

Formulations studied in the beagle dog.

| Component | HPMCAS (g) | Control (g) |
|---|---|---|
| Compound 1 (0.899 potency) | 0.389 | 0.389 |
| HPMCAS | 3.494 | — |
| 0.5% methyl cellulose solution | 210 | 210 |

TABLE 5-2

Canine pharmacokinetics after oral dosing of Compound 1 formulation.

| Formulation | Dose[1] (mg) | n[2] | $C_{max}$ (μg/ml) | $AUC_{0-24}$ (μg-hr/ml) |
|---|---|---|---|---|
| Control | 50 | 5 | 0.28 ± 0.16 (57)[3] | 0.59 ± 0.52 (88)[3] |
| HPMCAS | 50 | 4 | 0.37 ± 0.09 (24)[3] | 1.21 ± 0.32 (26)[3] |

[1]For comparison purposes, the average weight of beagle dogs used in this study was around 10 kg.
[2]Number of dogs studied.
[3]Coefficient of variation (%).

EXAMPLE 6

The drug Z-4-(3,4-dichlorophenyl)-2-[2-(4-methylpiperazin-1-yl)-benzylidene]-thiomorpholin-3-one hydrochloride monohydrate has a solubility of 3 mg/mL at pH 2, and a solubility of 0.012 mg/ml at pH 6.8. Dissolution performance was measured at 37° C. using a microcentrifuge method. For these tests, 2.7 mg drug in 0.9 mLs 25% gastric solution/75% HPLC water was added to each of 6 microcentrifuge tubes. At time 0, 0.9mLs 2×PBS without polymer was added to tubes 1 and 2, and 0.9 mLs 2×PBS containing 3.6 mg HPMCAS-MF or cellulose acetate trimellitate (CAT) was added to tubes 3 and 4, or 5 and 6. Samples were taken after 4, 10, 20, 40, 90, and 180 minutes, analyzed by HPLC, and compound concentrations were calculated. Gastric solution is 84 mM HCl, 34 mM NaCl, pH 1.2. PBS is phosphate buffered saline: 20 mM sodium phosphate, 4.7 mM potassium phosphate, 8.2 mM NaCl, 0.2 mM KCl, pH 6.5. "2×PBS" is a solution in which the components of PBS are present at 2-fold higher concentration. The data are summarized in Table 6-1.

TABLE 6-1

Dissolution Test Results

| Time (min) | Drug Conc (mcg/ml) Drug Alone | Drug Conc (mcg/ml) Drug/HPMCAS | Drug Conc (mcg/ml) Drug/CAT |
| --- | --- | --- | --- |
| 4 | 518 | 773 | 543 |
| 10 | 459 | 535 | 465 |
| 20 | 432 | 481 | 423 |
| 40 | 317 | 434 | 365 |
| 90 | 263 | 387 | 389 |
| 180 | 204 | 341 | 333 |

These data demonstrate that HPMCAS and CAT have the capacity to enhance the solubility of the studied drug. For example, at 180 minutes, the enhancement is greater than 1.5-fold, for HPMCAS and for CAT.

What is claimed is:

1. A composition comprising
   a) a basic drug, a drug which forms a zwitterion, or a salt of either, wherein said basic drug, zwitterionic drug, or salt of either is amorphous, admixed with
   b) a polymer selected from hydroxypropylmethylcellulose acetate succinate (HPMCAS), cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP);
      wherein said basic drug, zwitterionic drug, or salt of either has a dose to aqueous solubility ratio greater than 100 at pH 5.0 to 7.0;
      wherein, in the absence of said polymer, said basic drug, zwitterionic drug or salt has a solubility in a first aqueous use environment having a pH of 1.0 to 2.0 which is at least 3-fold the solubility of said drug in a second aqueous use environment having a pH in the range of 5.0 to 7.0;
   and wherein, in said composition, said polymer is present in an amount such that, at any time during the first two hours following the time at which said composition has been introduced from said first use environment into said second use environment, the concentration of said dissolved basic drug, zwitterionic drug, or salt of either in said second use environment is at least 1.5-fold the concentration of said dissolved basic drug, zwitterionic drug, or salt introduced from said first environment into said second environment in a control composition not containing said polymer.

2. A composition as defined in claim 1, wherein said use environment is the gastrointestinal tract.

3. A composition as defined in claim 1, wherein, said, use environment is in vitro aqueous test medium.

4. A composition as defined in claim 1, wherein said polymer increases the concentration of said dissolved basic drug, zwitterionic drug, or salt of either in said second use environment to at least 2-fold the concentration of said dissolved basic drug, zwitterionic drug, or salt introduced from said first environment into said second environment in a control composition not containing said polymer.

5. A composition as defined in claim 1, wherein said polymer increases the concentration of said dissolved basic drug, zwitterionic drug, or salt of either in said use environment to at least 5-fold the concentration of said dissolved basic drug, zwitterionic drug, or salt introduced from said first environment into said second environment in a control composition not containing said polymer.

6. A composition as defined in claim 1, wherein said polymer is selected from HPMCAS and CAT.

7. A composition as defined in claim 6, wherein said polymer is HPMCAS.

8. A composition comprising a basic drug, a zwitterionic drug, or a salt of either, wherein said basic drug, zwitterionic drug, or salt of either is amorphous, admixed with a polymer selected from hydroxypropylmethylcellulose acetate succinate (HPMCAS), cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP);
   wherein said basic drug, zwitteronic drug, or salt of either has a dose to aqueous solubility ratio greater than 100 at pH 5.0 to 7.0; and
   wherein, when said composition is dissolved in an aqueous in vitro test medium having a pH of 1.0 to 2.0, and said test medium is then adjusted to a pH between 5.0 and 7.0, the concentration of said drug in said aqueous pH 5–7 test medium, at any time during the first two hours following said pH adjustment, is at least 1.5-fold the concentration of said drug in a control aqueous test medium not containing said polymer.

9. A composition as defined in claim 8, wherein the concentration of said drug in said aqueous pH 5–7 test medium, at any time during the first two hours following said pH adjustment, is at least 2-fold the concentration of said drug in a control aqueous test medium not containing said polymer.

10. A composition as defined in claim 8, wherein the concentration of said drug in said aqueous pH 5–7 test medium, at any time during the first two hours following said pH adjustment, is at least 5-fold the concentration of said drug in a control aqueous test medium not containing said polymer.

11. A composition as defined in claim 8, wherein said polymer is selected from HPMCAS and CAT.

12. A composition as defined in claim 11, wherein said polymer is HPMCAS.

13. A composition comprising
   a basic drug, a drug which forms a zwitterion, or a salt of either, wherein said basic drug, zwitterionic drug, or salt of either is amorphous, admixed with
   a polymer selected from hydroxypropylmethylcellulose acetate succinate (HPMCAS), cellulose acetate trimellitate (CAT), hydroxypropylcellulose acetate phthalate (HPCAP), hydroxypropylmethyl cellulose acetate phthalate (HPMCAP), and methylcellulose acetate phthalate (MCAP);
   wherein said basic drug, zwitterionic drug, or salt of either has a dose to aqueous solubility ratio greater than 100 at pH 5.0 to 7.0;
   said composition effecting in vivo either a maximum drug concentration in serum or plasma of a test subject (Cmax) or an area under the curve (AUC) plotting the serum or plasma concentration of drug along the ordinate (Y-axis) against time along the abscissa (X-axis) that is at least 1.25 times the corresponding Cmax or AUC effected by a control composition comprising an equivalent quantity of drug and excipients, but without said polymer.

14. A composition as defined in claim 13, which effects a coefficient of variation of Cmax or AUC which is at least 10% less than the coefficient of variation of Cmax and/or AUC observed for said control composition.

15. A composition as defined in claim 13, wherein said Cmax or AUC of said polymer-containing composition is at least 1.5 times the corresponding control Cmax or AUC.

16. A composition as defined in claim 13, wherein the Cmax or AUC of said polymer-containing composition is at least 2.0 times the corresponding control Cmax or AUC.

17. A composition as defined in claim 13, wherein both said Cmax and AUC are at least 1.5 times the corresponding control Cmax and AUC.

18. A composition as defined in claim 14, wherein said coeffient of variation for both Cmax and AUC is at least 10% less than the corresponding coefficients of variation for Cmax and AUC observed for said control composition.

19. A composition as defined in claim 13, wherein said polymer is selected from HPMCAS and CAT.

20. A composition as defined in claim 19, wherein said polymer is HPMCAS.

21. A method of administering a basic drug, a drug which forms a zwitterion, or a salt of either, wherein said basic drug, zwitterionic drug, or salt of either is amorphous, comprising co-administering, to a patient in need of said drug:
 a) said basic drug, zwitterionic drug, or salt of either, wherein said basic drug, zwitterionic drug, or salt of either has a dose to aqueous solubility ratio greater than 100 at pH 5.0 to 7.0; and
 b) a polymer selected from hydroxypropylmethylcellulose acetate succinate (HPMCAS), cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP);
 wherein, in the absence of said polymer, said basic drug, zwitterionic drug or salt of either has a solubility in a first aqueous use environment having a pH of 1.0 to 2.0 which is at least 3-fold the solubility of said drug in a second aqueous use environment having a pH in the range of 5.0 to 7.0;
 and wherein said polymer is co-administered in an amount such that, at any time during the first two hours following the time at which said basic drug, zwitterionic drug, or salt of either has been introduced from said first use environment into said second use environment, the concentration of said basic drug, zwitterionic drug, or salt of either in said second use environment is increased to at least 1.5-fold the concentration of said basic drug, zwitterionic drug, or salt introduced from said first environment into said second environment in a control composition not containing said polymer.

22. A method as defined in claim 21, wherein said polymer increases the concentration of said dissolved basic drug, zwitterionic drug, or salt of either in said second use environment to at least 2-fold the concentration of said dissolved basic drug, zwitterionic drug, or salt introduced from said first environment into said second environment in a control composition not containing said polymer.

23. A method as defined in claim 21, wherein said polymer increases the concentration of said dissolved basic drug, zwitterionic drug, or salt of either in said second use environment to at least 5-fold the concentration of said dissolved basic drug, zwitterionic drug, or salt introduced from said first environment into said second environment in a control composition not containing said polymer.

24. A method as defined in claim 21, wherein said basic drug, zwitterionic drug, or salt of either is administered separately from said polymer.

25. A method as defined in claim 24, wherein said basic drug, zwitterionic drug, or salt of either and said polymer are administered at essentially the same time.

26. A method as defined in claim 21, wherein said basic drug, zwitterionic drug, or salt of either is administered in a composition also composing said polymer admixed therein.

27. A composition as defined in claim 21, wherein said polymer is selected from, HPMCAS and CAT.

28. A composition as defined in claim 27, wherein said polymer is HPMCAS.

29. A composition comprising
 a) a basic drug, a drug which forms a zwitterion, or a salt of either, wherein said basic drug, zwitterionic drug, or salt of either is crystalline, admixed with
 b) a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethyl-cellulose acetate phthalate (HPMCAP), and methylcellulose acetate phthalate (MCAP);
 wherein, in the absence of said polymer, said basic drug, zwitterionic drug or salt has a solubility in a first aqueous use environment having a pH of 1.0 to 2.0 which is at least 3-fold the solubility of said drug in a second aqueous use environment having a pH in the range of 5.0 to 7.0;
 and wherein, in said composition, said polymer is present in an amount such that, at any time during the first two hours following the time at which said composition has been introduced from said first use environment into said second use environment, the concentration of said dissolved basic drug, zwitterionic drug, or salt of either in said second use environment is at least 1.5-fold the concentration of said dissolved basic drug, zwitterionic drug, or salt introduced from said first environment into said second environment in a control composition not containing said polymer.

30. A composition comprising a basic drug, a zwitterionic drug, or a salt of either, wherein said basic drug, zwitterionic drug, or salt of either is crystalline, admixed with a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethyl-cellulose acetate phthalate (HPMCAP), and methylcellulose acetate phthalate (MCAP);
 wherein, when said composition is dissolved in an aqueous in vitro test medium having a pH of 1.0to 2.0, and said test medium is then adjusted to a pH between 5.0 and 7.0, the concentration of said drug in said aqueous pH 5–7 test medium, at any time during the first two hours following said pH adjustment, is at least 1.5-fold the concentration of said drug in a control aqueous test medium not containing said polymer.

31. A composition comprising
 a basic drug, a drug which forms a zwitterion, or a salt of either, wherein said basic drug, zwitterionic drug, or salt of either is crystalline, admixed with
 a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethyl cellulose acetate phthalate (HPMCAP), and methylcellulose acetate phthalate (MCAP);

said composition effecting in vivo either a maximum drug concentration in serum or plasma of a test subject (Cmax) or an area under the curve (AUC) plotting the serum or plasma concentration of drug along the ordinate (Y-axis) against time along the abscissa. (X-axis) that is at least 1.25 times the corresponding Cmax or AUC effected by a control composition comprising an equivalent quantity of drug and excipients, but without said polymer.

32. A method of administering a basic drug, a drug which forms a zwitterion, or a salt of either, wherein said basic drug, zwitterionic drug, or salt of either is crystalline, comprising co-administering, to a patient in need of said drug:

a) said basic drug, zwitterionic drug, or salt of either; and
b) a polymer selected from hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethyl-cellulose acetate phthalate (HPMCAP), and methylcellulose acetate phthalate (MCAP);

wherein, in the absence of said polymer, said basic drug, zwitterionic drug or salt of either has a solubility in a first aqueous use environment having a pH of 1.0 to 2.0 which is at least 3-fold the solubility of said drug in a second aqueous use environment having a pH in the range of 5.0 to 7.0;

and wherein said polymer is co-administered in an amount such that, at any time during the first two hours following the time at which said basic drug, zwitterionic drug, or salt of either has been introduced from said first use environment into said second use environment, the concentration of said basic drug, zwitterionic drug, or salt of either in said second use environment is increased to at least 1.5-fold the concentration of said basic drug, zwitterionic drug, or salt introduced from said first environment into said second environment in a control composition not containing said polymer.

33. A composition as defined in claim 29, wherein said basic drug, zwitterionic drug, or salt of either has a dose to aqueous solubility ratio greater than 100 at pH 5.0 to 7.0.

34. A composition as defined in claim 29, wherein said use environment is the gastrointestinal tract.

35. A composition as defined in claim 29, wherein said use environment is in vitro aqueous test medium.

36. A composition as defined in claim 29, wherein said polymer increases the concentration of said dissolved basic drug, zwitterionic drug, or salt of either in said second use environment to at least 2-fold the concentration of said dissolved basic drug, zwitterionic drug, or salt introduced from said first environment into said second environment in a control composition not containing said polymer.

37. A composition as defined in claim 29, wherein said polymer increases the concentration of said dissolved basic drug, zwitterionic drug, or salt of either in said second use environment to at least 5-fold the concentration of said dissolved basic drug, zwitterionic drug, or salt introduced from said first environment into said second environment in a control composition not containing said polymer.

38. A composition as defined in claim 29, wherein said polymer is selected from HPMCAS, CAT, and CAP.

39. A composition as defined in claim 38, wherein said polymer is HPMCAS.

40. A composition as defined in claim 30, wherein the concentration of said drug in said aqueous pH 5–7 test medium, at any time during the first two hours following said pH adjustment, is at least 2-fold the concentration of said drug in a control aqueous test medium not containing said polymer.

41. A composition as defined in claim 30, wherein the concentration of said drug in said aqueous pH 5–7 test medium, at any time during the first two hours following said pH adjustment, is at least 5-fold the concentration of said drug in a control aqueous test medium not containing said polymer.

42. A composition as defined in claim 30, wherein said basic drug, zwitterionic drug, or salt of either has a dose to aqueous solubility ratio greater than 100 at pH 6.5.

43. A composition as defined in claim 30, wherein said polymer is selected from HPMCAS, CAT, and CAP.

44. A composition as defined in claim 43, wherein said polymer is HPMCAS.

45. A composition as defined in claim 31, which effects a coefficient of variation of Cmax or AUC which is at least 10% less than the coefficient of variation of Cmax and/or AUC observed for said control composition.

46. A composition as defined in claim 31, wherein said Cmax or AUC of said polymer-containing composition is at least 1.5 times the corresponding control Cmax or AUC.

47. A composition as defined in claim 31, wherein the Cmax or AUC of said polymer-containing composition is at least 2.0 times the corresponding control Cmax or AUC.

48. A composition as defined in claim 31, wherein both said Cmax and AUC are at least 1.5 times the corresponding control Cmax and AUC.

49. A composition as defined in claim 45, wherein said coeffient of variation for both Cmax and AUC is at least 10% less than the corresponding coefficients of variation for Cmax and AUC observed for said control composition.

50. A composition described in claim 31, wherein said basic drug, zwitterionic drug, or salt of either has a dose to aqueous solubility ratio greater than 100 at pH 6.5.

51. A composition as defined in claim 31, wherein said polymer is selected from HPMCAS, CAT, and CAP.

52. A composition as defined in claim 51, wherein said polymer is HPMCAS.

53. A method as defined in claim 32, wherein said polymer increases the concentration of said dissolved basic drug, zwitterionic drug, or salt of either in said second use environment to at least 2-fold the concentration of said dissolved basic drug, zwitterionic drug, or salt introduced from said first environment into said second environment in a control composition not containing said polymer.

54. A method as defined in claim 32, wherein said polymer increases the concentration of said dissolved basic drug, zwitterionic drug, or salt of either in said second use environment to at least 5-fold the concentration of said dissolved basic drug, zwitterionic drug, or salt introduced from said first environment into said second environment in a control composition not containing said polymer.

55. A method as defined in claim 32, wherein said basic drug, zwitterionic drug, or salt of either is administered separately from said polymer.

56. A method as defined in claim 55, wherein said basic drug, zwitterionic drug, or salt of either and said polymer are administered at essentially the same time.

57. A method as defined in claim 32, wherein said basic drug, zwitteronic drug, or salt of either is administered in a composition also comprising said polymer admixed therein.

58. A composition as described in claim 32, wherein said basic drug, zwitterionic drug, or salt of either has a dose to aqueous solubility ratio greater than 100 at pH 6.5.

59. A composition as defined in claim 32, wherein said polymer is selected from HPMCAS, CAT, and CAP.

60. A composition as defined in claim 59, wherein said polymer is HPMCAS.

* * * * *